United States Patent [19]

Heyman

[11] 4,331,422
[45] May 25, 1982

[54] ACOUSTIC TOOTH CLEANER

[75] Inventor: Joseph S. Heyman, Gloucester, Va.

[73] Assignee: The United States of America as represented by the Administrator of the National Aeronautics and Space Administration, Washington, D.C.

[21] Appl. No.: 178,193

[22] Filed: Aug. 14, 1980

[51] Int. Cl.³ .................................................. A61C 3/06
[52] U.S. Cl. .................................... 433/125; 433/118; 433/86; 128/62 A
[58] Field of Search .................. 433/125, 119, 118, 86

[56] References Cited

U.S. PATENT DOCUMENTS 2,612,732 10/1952 Ziegler ................................ 433/125
3,636,947 1/1972 Balamuth ........................... 128/62 A

FOREIGN PATENT DOCUMENTS 2442466 3/1976 Fed. Rep. of Germany ........ 433/86

Primary Examiner—Robert Peshock
Attorney, Agent, or Firm—William H. King; John R. Manning; Howard J. Osborn

[57] ABSTRACT

This invention is an acoustic oral hygiene unit that uses acoustic energy to oscillate mild abrasive particles 17a in a water suspension 17 which is then directed in a low pressure stream onto the teeth. The oscillating abrasives scrub the teeth clean removing food particles, plaque, calculous, and other foreign material from tooth surfaces, interproximal areas, and tooth-gingiva interface more effectively than any previous technique. The relatively low power output and the basic design makes the invention safe and convenient for everyday use in the home without special training. This invention replaces all former means of home dental prophylaxis, and requires no augmentation to fulfill all requirements for daily oral hygienic care.

3 Claims, 2 Drawing Figures

U.S. Patent     May 25, 1982     4,331,422
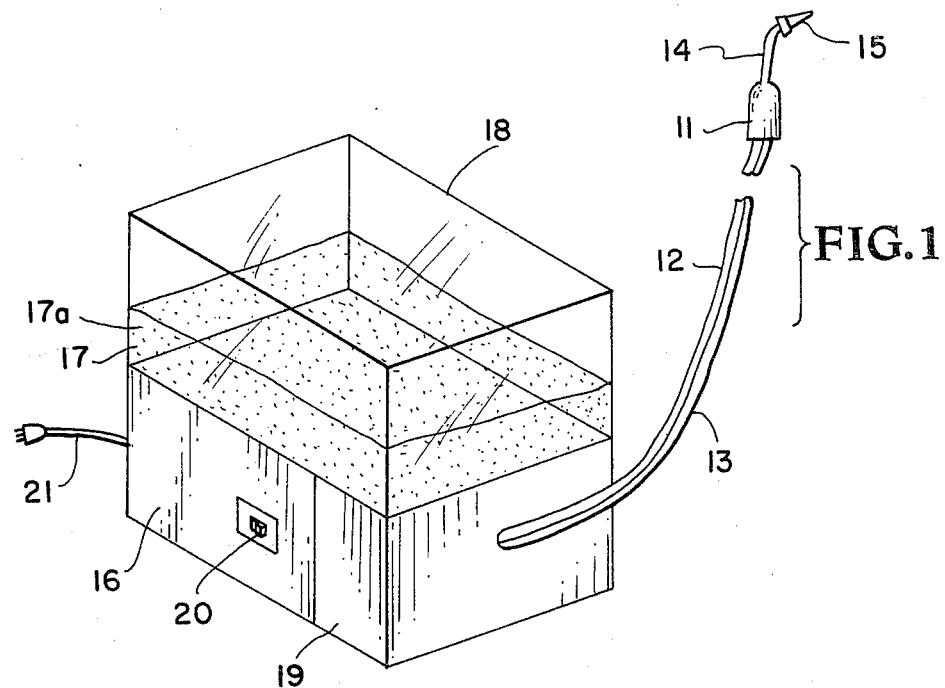
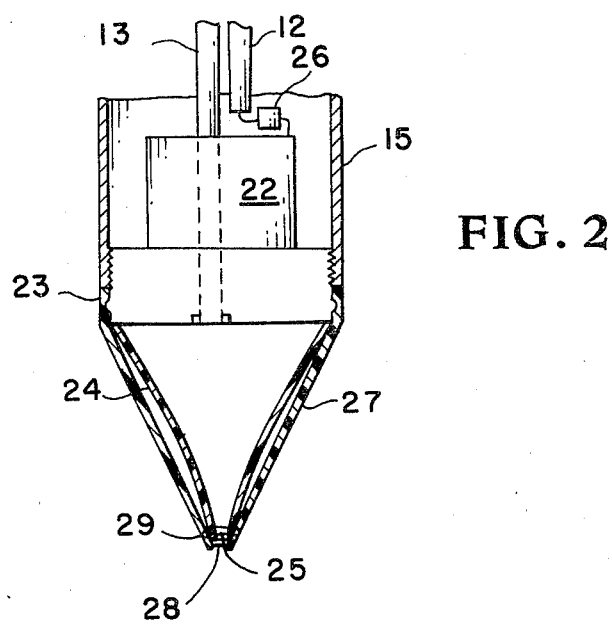

ACOUSTIC TOOTH CLEANER

ORIGIN OF THE INVENTION

The invention described herein was made by an employee of the United States Government and may be used by or for the Government for governmental purposes without the payment of any royalties thereon or therefor.

BACKGROUND OF THE INVENTION

This invention relates generally to oral hygienic care, and more specifically to methods and apparatus utilizing acoustically oscillated abrasives entrained in a low pressure water stream for removal of foreign material from the teeth and treatment of gingival tissues in the prevention of periodontal disease.

Periodontal disease is widespread throughout the world, and is the major cause of tooth loss in persons 35 years and older. Periodontal disease can also lead to more serious consequences including degeneration of alveolar bone structure, and serious infection. The incidence of dental caries and associated periodontal disease is a function of the presence of food particles and other oral debris and dental plaque in close contact with and between the teeth over a period of time. The most effective means of combating the rising incidence of periodontal disease is through education of the public in the practice of proper dental prophylaxis, and the provision of effective instruments to aid them in removal of food debris and plaque necessary in maintaining good oral hygiene.

In the field of home dental prophylaxis, mechanical brushing with a dentifrice is the conventional and most widely used technique for daily removal of oral debris and plaque buildup. Brushing is augmented to some extent by flossing and more recently through use of a pulsed, high pressure water jet to facilitate removal of particles between teeth and in inaccessible reaches of the mouth. Mechanical brushing, however, is a time consuming process if properly done, and motivation to maintain a proper daily regimen, including brushing, flossing and water jet cleaning is difficult to instill. Furthermore, because of the irregular topography of the teeth, inaccessibility of some areas, manual dexterity required, and difficult gingival tooth interface area, these conventional techniques are not fully effective. Mechanical brushing does not clean between teeth, nor at the gingival interface; flossing will remove particles between teeth, but does not affect plaque; and water jet rinses away oral debris in inaccessible areas of the mouth, between teeth, and at the gum line, but does not remove plaque. The high pressure of the water jet, 60 to 90 psi, may also damage gums and lead to dangerous tooth gum separation. Due to the demands of the regimen and the limitations of the instruments and techniques, the brushing, flossing and water jet system does not provide the most efficacious results in oral hygiene.

Improvements to the basic cleaning system have been added from time to time. Power driven tooth brushes have reduced the need for manual dexterity and have improved brushing time and gum massage, however, they still do nothing about deposits of plaque and debris between teeth, and flossing is still necessary.

Acoustic cleaning, in particular ultrasonics, has been widely utilized in industrial cleaning applications for many years, and there have been numerous attempts to apply similar techniques to the cleaning of teeth with varying degrees of success. There have been three basic approaches to utilizing ultrasonic energy for dental care. The simplest is the ultrasonic toothbrush which consists essentially of a normal power driven toothbrush head oscillated at ultrasonic frequencies. This device improves cleaning, stain removal, and gum massage, but does not reach the areas between teeth. Another development is the ultrasonic scaler. In this device, electrical energy and water are fed to a handpiece. The handpiece contains a magnetostrictive element to convert the alternating electrical current into high frequency mechanical vibrations. These ultrasonic vibrations are coupled to a thin metal scaling tip resulting in a linear tip motion of from 0.08 to 0.3 mm at the frequency of typically 16,000 to 40,000 Hz. The water fed into the handpiece is used to cool the magnetostrictive element and is then directed in a stream onto the vibrating scaling tip. The water sprayed onto the tip is atomized by the rapid vibrations, and a caviatation action produced in the vicinity of the tip will remove plaque and calculus. Although this method of plaque removal is highly effective, the high energy generated by the oscillating scaling tip can be dangerous and use of ultrasonic scaling devices must be left to trained professional dental personnel. If tip pressure is excessive severe damage can result including denudation of alveolar bone, damage to tooth buds, sequestrum of the maxilla, pathalogic fractures, and root surface damage. Contact of the scaling tip with gums can cause painful lacerations. The potential dangers of improper use make the ultrasonic scalers entirely inappropriate home prophylaxis.

The third method normally employed introduces ultrasonic energy directly into a stream of water. At high power levels, this ultrasonic energy produces cavitation within the waterstream itself. This stream can then be pulsed or steady streamed onto the teeth and the collapsing cavitation bubbles produce intense pressure shocks which break away plaque through a microfatiguing action. However, the high pressure generated by cavitation can lead to erosion of tooth surfaces, and there is some evidence that nerve damage may result.

There are also devices which operate on a similar basis as the water jet previously described. These instruments project a concentrated, high pressure, slurry consisting of abrasives suspended in water, impacts upon the teeth at high velocity and the kinetic energy of the high velocity abrasives impacting on the plaque effectively removes it. This system, like the water jet, requires a high pressure stream which can cause gingival damage and accelerate tooth-gum separation, and is best not used for regular home care.

The present invention utilizes acoustically oscillated abrasive particles in a low pressure waterstream to create a scrubbing action. The scrubbing action of the abrasive particles effectively removes plaque, calculus, and food particles from teeth surfaces between teeth, and in the gingival interproximal area. It also stimulates gums and flushes particles from inaccessible areas of the mouth. The invention provides complete home dental care and does not require augmentation by flossing, water jet, etc. It is simple and easy to use, requires little manual dexterity, and is entirely safe. Thus, in accordance with this invention, the desired results of all the oral hygenic devices and techniques of the prior art are achieved without the usual attending disadvantages, by a new and novel system that is superior to any other available for daily prophylactic dental care in the home.

It is therefore an object of this invention to provide an improved method and apparatus for daily oral hygiene utilizing acoustic energy.

A further object of this invention is to provide a technique and apparatus completely safe and easy to use by adults and children in the home on a regular basis.

Another object of the present invention is to provide improved cleaning of plaque, calculus, and particles from hard to reach interproximal and gumline areas in one operation.

Other objects and advantages of this invention will become readily apparent hereinafter in the specification and drawings.

SUMMARY OF THE INVENTION

This invention consists essentially of a method for obtaining comprehensive prophylactic dental care and an apparatus for utilizing said method. The method consists of suspending mild abrasive particles in water, and pumping the water abrasive suspension at low pressure to a handpiece where acoustic energy is applied to the suspension. This acoustic energy is transferred through the water to the abrasive particles and imparts to them an oscillatory motion. The oscillating motion of the abrasives is then amplified, and the energized water abrasive suspension is directed in a low pressure stream so as to impinge upon the teeth and gums. The oscillating motion of the abrasive particles in and around the teeth remove food particles, plaque, calculus, and other undesirable oral cavity contaminants from even difficult interproximal and gum line areas, and the low pressure water stream flushes them away.

The apparatus whereby this method is carried out consists of a tank to hold the abrasive water suspension, a pump means whereby the suspension is drawn from the tank and delivered under pressure through a hollow flexible tube to a handpiece. The handpiece itself has an outer insulating housing means which contains and supports an acoustic transducer either piezoelectric, magnetostrictive, or electromagnetic. This transducer is bonded to a ¼ wave impedance matching plate. A high frequency, low power electrical signal is provided by suitable trnsformer circuit means through an insulated power line to the handpiece. The electrical signal provided is applied to the transducer through suitable electrical impedance matching means thus exiting the transducer.

The matching plate is connected to a hollow exponentially-tapered acoustic amplifying cone. The tube delivering the pressurized water abrasive suspension passes through a hole in the transducer and bonded matching plate, and discharges into the amplifier cone. The amplifier cone has a samll hole at the end to reduce the water flow and to deliver the energized suspension to the oral cavity. An outer cone attaches to the handpiece and covers the amplifying cone, protecting it, and insulating the cone from contact with the user's mouth. The protecting cone contains an "O"-ring to seal the air space between the two cones and prevent the suspension from filling the space. The outer cone has a hole in the end concentric to the hole in the amplifier cone permitting the energized suspension stream to pass out of the handpiece and into the mouth unperturbed.

BRIEF DESCRIPTION OF THE DRAWINGS

FIG. 1 is a perspective view of the acoustic dental hygiene unit embodying the present invention; and FIG. 2 is a side view, partly in cross-section, of the acoustic tip, of the dental hygiene unit according to the present invention.

DETAILED DESCRIPTION OF THE INVENTION

A general embodiment of the invention is shown in a perspective view of FIG. 1. The invention includes an electrically insulating handle 11 adapted to be comfortably held by the user and to protect him from electrical shock. The handle is attached to electrically shielded supply means 12 which supplies electrical power through handle 11 and to fluid supply means 13 which supplies a constant flow of fluid through handle 11. Applicator 14 extends from the opposite end of handle 11 and has at its end an acoustic wand tip 15. The electrical supply means 12 powers an acoustic transducer 22 (see FIG. 2) in the acoustic wand tip 15. The fluid supplied by fluid supply means 13 passes through transducer 22 and is acted upon by the acoustic energy created by tranducer 22 before passing out of the acoustic wand tip 15 into the mouth.

The pressure and velocity of the fluid stream in supply means 13 is controlled by a pump 16. The fluid supply is a liquid 17 with mild abrasive particles 17a suspended therein. The fluid is contained in a reservoir 18 and is pumped by pump 16 either continuously or intermittently. A driver means 19 is provided for converting normal house current, 60 Hz 110/120 volt, into current of proper frequency and voltage for use with acoustic transducer 22. The abrasive particles 17a can be the standard dental abrasives such as found in tooth pastes or tooth powders as well as any abrasive smaller than the acoustic wavelength. The most general dental abrasive is zirconium silicate with particle sizes typically 25–60 micrometers. Controlled size sand could also be used as particles, 17a.

The invention is powered through a normal electrical plug and cord 21 which provides 60 Hz 110/120 volt AC current to both the pump 16 and driver means 19 simultaneously by operation of an electrical switch 20.

Turning now to FIG. 2 there is a side view of the acoustic wand tip 15 partly in section. The acoustic transducer 22 is, for example, either a piezoelectric, magnetostrictive, or electromagnetic acoustic transducer. This transducer is bonded to a ¼ wave impedance matching plate 23 having an acoustic impedance, Z (plate), such that Z (plate) = (Z(transducer) x Z (water))$^{\frac{1}{2}}$ where Z equals the product of the sound velocity times the density. The acoustic transducer 22 and the bonded impedance matching plate 23 have a passage through them such that the fluid supply means 13 passes through them and empties into a hollow, exponentially tapered acoustic amplitude amplifier cone 24 which is bonded to the ¼ wave impedance matching plate 23. An orifice 25 at the small end of the tapered amplifying cone 24 reduces the waterflow rate and directs the fluid abrasive suspension in a stream as it passes out of the acoustic wand tip and onto the teeth and gums.

The electrical supply means 12, transmits the high frequency electrical signal generated by the driver means 19 to the acoustic wand tip where the signal is applied to the acoustic transducer 22 through an electrical impedance matching means 26. A hollow hygienic cone 27 snaps over the amplifying cone 24 leaving an insulating air space between the surfaces of the two cones. The hygienic cone 27 has at its tip an orifice 28 such that when snapped in place the orifice 28 in the hygienic cone 27 and the orifice 25 in the amplifying cone 24 are concentric and the hygienic cone orifice 28 does not interfere with the fluid stream passing out of the wand tip. The hygienic cone 27 has a small O-ring 29 bonded to the inside surface of the cone concentric with its orifice 28 such that when the hygienic cone 27 is snapped in place the O-ring is sealingly in contact with the outer surface of the amplifying cone 24 preventing the air space between the two cones from filling with fluid. The hygienic cone 27 provides for personal hygiene between users with each user having his own cone.

In operation, the current supply source 21 is attached electrically to a standard 60 Hz, 110/120 volt outlet and the electrical switch means 20 is moved to the "ON" position. This simultaneously energizes the pump 16, driver means 19, and the acoustic transducer 22. The water abrasive suspension 17 is drawn from the reservoir means 18 and pumped under pressure through fluid supply means 13 to the acoustic wand tip 15 in either a steady stream or a pulsed stream by the pump 16.

Driver means 19 converts the 60 Hz 110/120 volt supply current into a high frequency signal of suitable voltage for use by acoustic transducer 22. The high frequency signal generated is transmitted through electrical supply means 12, in this embodiment an electrically shielded conductive wire, to the acoustic transducer 22 through the electrical impedance matching means 26. The acoustic transducer 22 is driven by the high frequency impedance matched signal with the ¼ wave impedance matching plate 23 acting as a ground plane.

The water abrasive suspension passes from the fluid supply 13 into the hollow exponentially tapered cone 24 which fills with the fluid. The high frequency electrical driver signal is converted to high frequency acoustic energy by the acoustic transducer 22 and the acoustic energy is transmitted by the ¼ wave plate 23 through the water in the amplifier cone 24. The amplifier cone 24 increases the amplitude of the acoustic waves in the water on a ratio inversely proportional to the diameter of the cone with total amplifier gain equaling the ratio of the diameter of the large end of the cone to the diameter of the small end of the cone. The acoustic energy waves traveling through the water in the cone impart energy to the suspended abrasive particles imparting a rapid oscillating motion to them, with the amplitude of oscillation increasing as the particles in the water suspension pass from the large end of the amplifying cone 24 to the small end.

The handle 11 is grasped by the user and the applicator 14 is used to position the acoustic wand tip 15 within the oral cavity and to direct the stream of acoustically energized abrasive particles and water suspension at the teeth and gingival tissue. The handle 11 is manipulated by the user in a manner such that all of the teeth and gingival areas are subjected to the cleansing action.

The acoustically energized, oscillating abrasive particles and water suspension pass out of the acoustic wand tip through the orifices 25 and 28, respectively, in the ends of the amplifier cone 24 and hygienic cone 27 in a stream of relatively small cross-sectional area and onto the teeth and gums. The low power, oscillatory nature of the acoustic waves and entrained abrasive particles will result in a scrubbing action to remove food deposits, plaque, and stains without harmful cavitation effects. Further, the acoustic waves will beneficially stimulate gingival tissues as will the kinetic energy of the stream if it is pulsed.

The abrasive particles used are chosen for configuration and hardness so as to ensure cleaning of the teeth and gums without harmful effects. Similarly, the pressure at which the pulsed or continuous stream is pumped from the wand tip is kept low, in the range of 10 to 40 psi to prevent harmful tooth-gum separation and "sandblasting" effect. The power level of the acoustic energy wave introduced into the stream is kept lower than cavitation level to prevent the harmful stressing created by the intense pressure of the collapsing cavitation bubbles. For daily care the acoustic energy can be set rather low and the abrasive hardness chosen to be just greater than that for plaque. However, for the removal of calculous, higher power and tooth cleaner type abrasives (standard dental material) should be used.

The advantages of this invention over those of the prior art are the provision of a safe, convenient method and device for comprehensive oral hygiene care in the home by users without special dental training.

The foregoing disclosure relates only to a preferred general embodiment of the present invention and many modifications and variations of the present invention are possible in light of the above teachings without departing from the spirit and scope of the invention as set forth in the appended claims.

What is claimed as new and desired to be secured by Letters Patent of the United States is:

1. A device for treatment of tooth and gingival structures to provide daily personal hygenic care comprising:
    a reservoir of a liquid;
    means for transmitting said liquid under pressure from said reservoir to an oral cavity;
    said means for transmitting said liquid includes a cone shaped cavity with the liquid flowing into the large end of said cavity and out of a small hole at the small end of said cavity into said oral cavity whereby the liquid under pressure keeps said cone shaped cavity filled with said liquid;
    an acoustic transducer supplied with a high frequency electrical signal;
    an impedance matching plate bonded to said acoustic transducer and enclosing the large end of said cavity whereby said acoustic transducer imparts through said impedance matching plate a back and forth motion to said liquid before it enters said oral cavity and said back and forth motion is mechanically amplified in said cone shaped cavity.

2. A device for treatment of tooth and gingival structures according to claim 1 wherein the sides of the cone shaped cavity are exponentially tapered to increase the amplification of said cone shaped cavity.

3. A device for treatment of tooth and gingival structures according to claim 1 wherein said liquid includes mild abrasive particles suspended therein whereby said back and forth motion is imparted to said particles.

* * * * *